US012577270B2

(12) United States Patent
Von Borstel et al.

(10) Patent No.: US 12,577,270 B2
(45) Date of Patent: Mar. 17, 2026

(54) 2',3'-DIACETYLURIDINE SUBSTITUTED WITH ACETOACETYL AT THE 5' POSITION

(71) Applicant: PHARMA CINQ, LLC, Rockville, MD (US)

(72) Inventors: Reid Warren Von Borstel, Potomac, MD (US); David Michael Simpson, North Bethesda, MD (US); Rolando Alejandro Garcia Garcia, Germantown, MD (US)

(73) Assignee: PHARMA CINQ, LLC, Rockville, MD (US)

( * ) Notice: Subject to any disclaimer, the term of this patent is extended or adjusted under 35 U.S.C. 154(b) by 417 days.

(21) Appl. No.: 18/021,907

(22) PCT Filed: Sep. 14, 2021

(86) PCT No.: PCT/US2021/050149
§ 371 (c)(1),
(2) Date: Feb. 17, 2023

(87) PCT Pub. No.: WO2022/056428
PCT Pub. Date: Mar. 17, 2022

(65) Prior Publication Data

US 2023/0357304 A1 Nov. 9, 2023

Related U.S. Application Data

(60) Provisional application No. 63/231,825, filed on Aug. 11, 2021, provisional application No. 63/227,611, filed on Jul. 30, 2021, provisional application No. 63/188,559, filed on May 14, 2021, provisional application No. 63/077,760, filed on Sep. 14, 2020.

(51) Int. Cl.
*C07H 19/067* (2006.01)

(52) U.S. Cl.
CPC .................................. *C07H 19/067* (2013.01)

(58) Field of Classification Search
None
See application file for complete search history.

(56) References Cited

U.S. PATENT DOCUMENTS

| | | | |
|---|---|---|---|
| 5,585,512 | A | 12/1996 | Yamazaki et al. |
| 7,709,459 | B2 | 5/2010 | von Borstel et al. |
| 7,915,233 | B1 | 3/2011 | Von Borstel |
| 9,566,257 | B2 | 2/2017 | Jalan et al. |
| 2001/0025032 | A1 | 9/2001 | Von Borstel et al. |
| 2004/0102523 | A1 | 5/2004 | Broquaire et al. |
| 2012/0259016 | A1 | 10/2012 | Jalan et al. |
| 2014/0142186 | A1 | 5/2014 | Scharschmidt et al. |
| 2018/0318381 | A1 | 11/2018 | Vockley et al. |
| 2023/0416292 | A1 | 12/2023 | Garcia Garcia et al. |
| 2024/0158431 | A1 | 5/2024 | Von Borstel et al. |

FOREIGN PATENT DOCUMENTS

| | | | |
|---|---|---|---|
| CN | 1031536 | A | 3/1989 |
| EA | 018007 | B1 | 4/2013 |
| EP | 3335735 | A1 | 6/2018 |
| JP | 2002-523434 | A | 7/2002 |
| JP | 2007-510734 | A | 4/2007 |
| KR | 100818202 | B1 | 3/2008 |
| RU | 2659388 | C1 | 7/2018 |
| WO | 2000/050043 | A1 | 8/2000 |
| WO | 2013/012760 | A1 | 1/2013 |
| WO | 2014/160502 | A1 | 10/2014 |
| WO | 2016/028894 | A1 | 2/2016 |
| WO | 2019/152776 | A1 | 8/2019 |
| WO | 2022/056428 | A1 | 3/2022 |
| WO | 2022/089612 | A1 | 5/2022 |
| WO | 2022/119784 | A1 | 6/2022 |
| WO | 2022/177740 | A1 | 8/2022 |

OTHER PUBLICATIONS

Ashour et al., "5-(m-Benzyloxybenzyl)barbituric acid acyclonucleoside, a uridine phosphorylase inhibitor, and 2', 3',5'-tri-O-acetyluridine, a prodrug of uridine, as modulators of plasma uridine concentration. Implications for chemotherapy," Biochemical Pharmacology, 51(12):1601-1611 (1996).
Database PubChem, PubChem CID: 9913736, Available Date: Oct. 25, 2006. <https://pubchem.ncbi.nlm.nih.gov/compound/9913736>.
McGregor et al., "Alkaline Bromine Oxidation of Amino Acids and Peptides: Formation of a-Ketoacyl Peptides and Their Cleavage by Hydrogen Peroxide," Biochemistry 1(1):53-60 (1962).
International Search Report issued in PCT/US2021/050149, dated Dec. 23, 2021.
International Search Report issued in PCT/US2021/061053, dated Feb. 7, 2022.
International Search Report issued in PCT/US2022/014874, dated May 6, 2022.
PubChem, Substance Record for SID 45985391, available date: Dec. 5, 2007. https://pubchem.ncbi.nlm.nih.gov/substance/45985391.
PubChem, Substance Record for SID 47237025, available date: Jun. 22, 2015. https://pubchem.ncbi.nlm.nih.gov/substance/47237025.

(Continued)

*Primary Examiner* — Traviss C McIntosh, III
(74) *Attorney, Agent, or Firm* — MEDLER FERRO WOODHOUSE & MILLS

(57) ABSTRACT

5'-O-(Acetoacetyl)-2',3'-di-O-acetyluridine is useful in the treatment or prevention of disorders characterized by cerebral metabolic energy failure or diminished mitochondrial energy reserve capacity.

29 Claims, 8 Drawing Sheets

(56) References Cited

OTHER PUBLICATIONS

Caldovic et al., "Genotype-Phenotype Correlations in Ornithine Transcarbamylase Deficiency: A Mutation Update," Journal of Genetics and Genomics 42:181-194 (2015).
Chinese Application No. 202011196732.4, filed Oct. 30, 2020.
Kubasov et al., "Chemical kinetics and catalysis. Part 1," Moscow University Publishing House: 2-3 (2004).
Livingston et al., "Body surface area prediction in normal-weight and obese patients", American Journal of Physiology—Endocrinology and Metabolism 281:E586-E591 (2001).
Mosley et al., "Mutant Clone of Chinese Hamster Ovary Cells Lacking 3-Hydroxy-3-methylglutaryl Coenzyme A Reductase," The Journal of Biological Chemistry 258(22):13875-13881 (1983).
Non-Final Office Action dated Sep. 22, 2025, in U.S. Appl. No. 18/036,744.
Novosibirsk, "Fundamentals of medical prevention," Educational and Methodical Manual for Students and Cadets of Advanced Training Cycles of State Professional Educational Institutions UDC 614.2-084, BBK 51.1(2)2:13-21 (2016).
Oxford English Dictionary, definition of "prevent"; accessed Sep. 9, 2025.
Smith et al., "Organic synthesis. Science and Art," Moscow Mir 573:64 (2001).
Zheng et al., "Production of N-acetylglucosamine by Biosynthesis," Beijing University of Chemical Technology: A Master's Thesis (2019).
Latvijas PSR Zinatnu akademijas vestis, Kimijas serija: 745-746 (1977).
Non-Final Office Action in U.S. Appl. No. 18/547,053, dated Dec. 19, 2025.

2',3'-DIACETYLURIDINE SUBSTITUTED WITH ACETOACETYL AT THE 5' POSITION

Oral delivery of uridine for therapeutic purposes is limited by its poor bioavailability, approximately 7% in both humans and mice. Ester prodrugs of uridine have been found to improve its bioavailability, though only one, 2',3',5,-tri-O-acetyluridine (or uridine triacetate) has been found adequate to deliver sufficient uridine for clinical purposes. The bioavailability of oral uridine triacetate has been measured at approximately 50% (Ashour 1996). There is therefore room for improvement in the efficiency of uridine delivery, which is important in that relatively large doses of uridine are required for it therapeutic applications.

SUMMARY OF THE INVENTION

This invention provides the compound 5'-O-(Acetoacetyl)-2',3'-di-O-acetyluridine. It provides a method of treating or preventing a disorder characterized by cerebral metabolic energy failure or diminished mitochondrial energy reserve capacity in a mammalian subject, comprising administering to the subject an amount of a compound of this invention effective to treat the disorder. This invention also provides a compound of this invention for use in treating or preventing, or for the manufacture of a medicament for treating or preventing, a disorder characterized by cerebral metabolic energy failure or diminished mitochondrial energy reserve capacity in a mammalian subject. And it provides a pharmaceutical composition comprising a compound of this invention and a pharmaceutically acceptable carrier. This invention also provides a method for producing 5'-O-Acetoacetyl-2',3'-di-O-acetyluridine, comprising the steps of: (a) mixing 2',3'-O-isopropylideneuridine and 2,2,6-trimethyl-4H-1,3-dioxin-4-one in dimethylformamide under conditions to produce 5'-O-acetoacetyl-2',3'-O-isopropylideneuridine; (b) mixing the 5'-O-acetoacetyl-2',3'-O-isopropylideneuridine from step (a) with aqueous acetic acid under conditions to produce crude 5'-O-Acetoacetyluridine; (c) dissolving the crude 5'-O-Acetoacetyluridine from step (b) in a mixture of dichloromethane and pyridine, and then adding acetic anhydride and stirring for several days; (d) to the mixture resulting from step (c), switch the solvent to ethyl acetate and neutralize with saturated $NaHCO_3$ to yield crude 5'-O-Acetoacetyl-2',3'-di-O-acetyluridine. This invention also provides 5'-O-Acetoacetyluridine as a crude intermediate and as an isolated compound.

The acetate substituents improve absorption from the gastrointestinal tract into the circulation, and are rapidly removed by nonspecific esterase activity. Acetate is a benign metabolite, but is pharmacologically and therapeutically neutral. The finding that the introduction of an acetoacetyl substituent at the 5' position improves uridine bioavailability sufficiently for therapeutic purposes in addition to having beneficial pharmacological activity in disorders for which uridine delivery is also indicated, yielding dual therapeutic activity in a single molecule, is an important advance.

Tri-AcAcU=2',3',5'-tri-O-(acetoacetyl)uridine

AcAcDAU=5'-O-(acetoacetyl)-2',3'-di-O-acetyluridine

DA-HU=2',3'-di-O-acetyl-5'-O-heptanoyluridine

Figure 2:
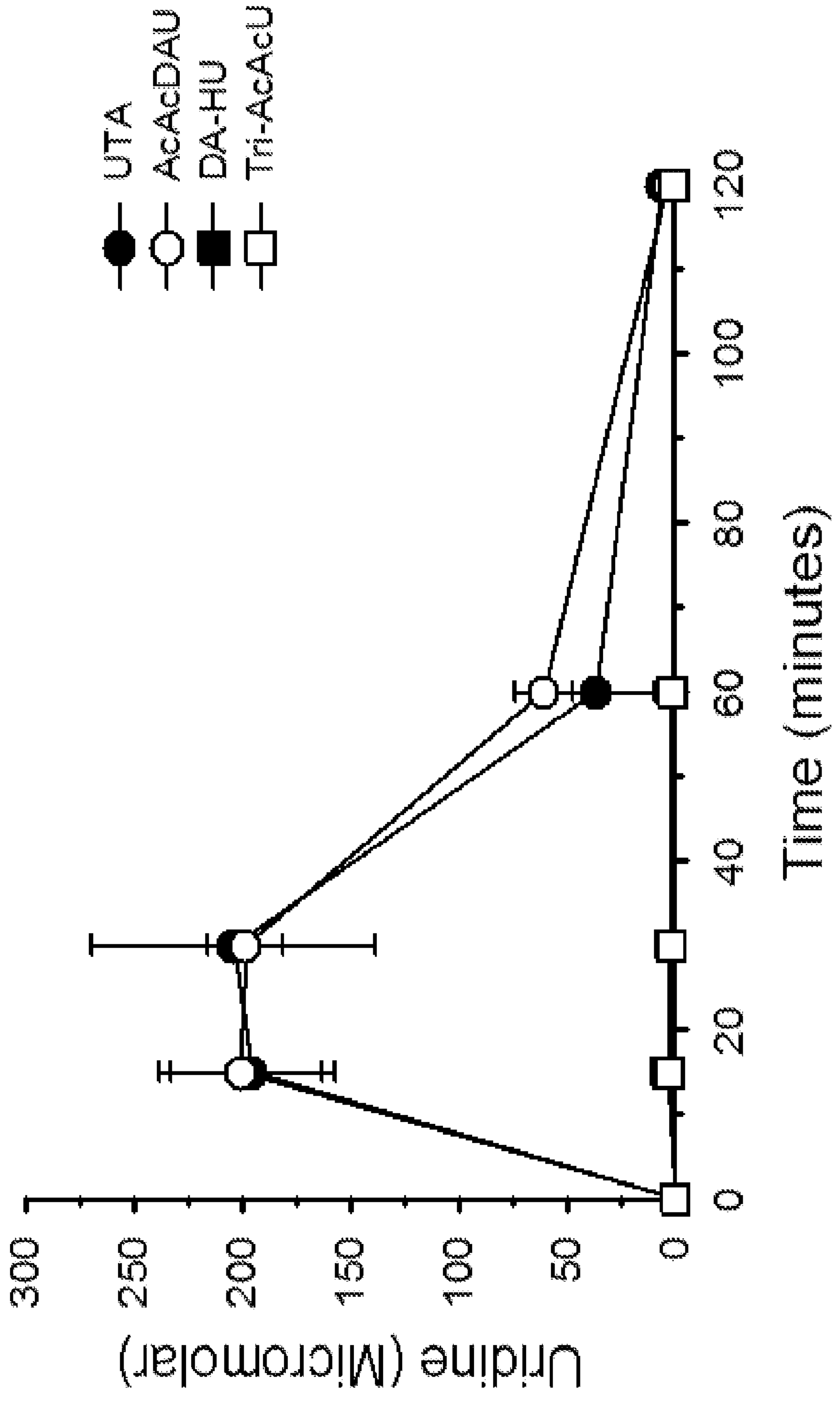

FIG. 2. Plasma uridine in mice after oral administration of uridine prodrugs Tri-AcAcU=2',3',5'-tri-O-(acetoacetyl)uridine AcAcDAU=5'-O-(acetoacetyl)-2',3'-di-O-acetyluridine DA-HU=2',3'-di-O-acetyl-5'-O-heptanoyluridine FIG. 3: Plasma uridine in mice after oral administration of uridine prodrugs UTA=uridine triacetate (2',3',5'-tri-O-acetyluridine)

DAU=2',3'-di-O-acetyluridine

AcAcU=5'-O-(acetoacetyl)uridine

Figure 4:
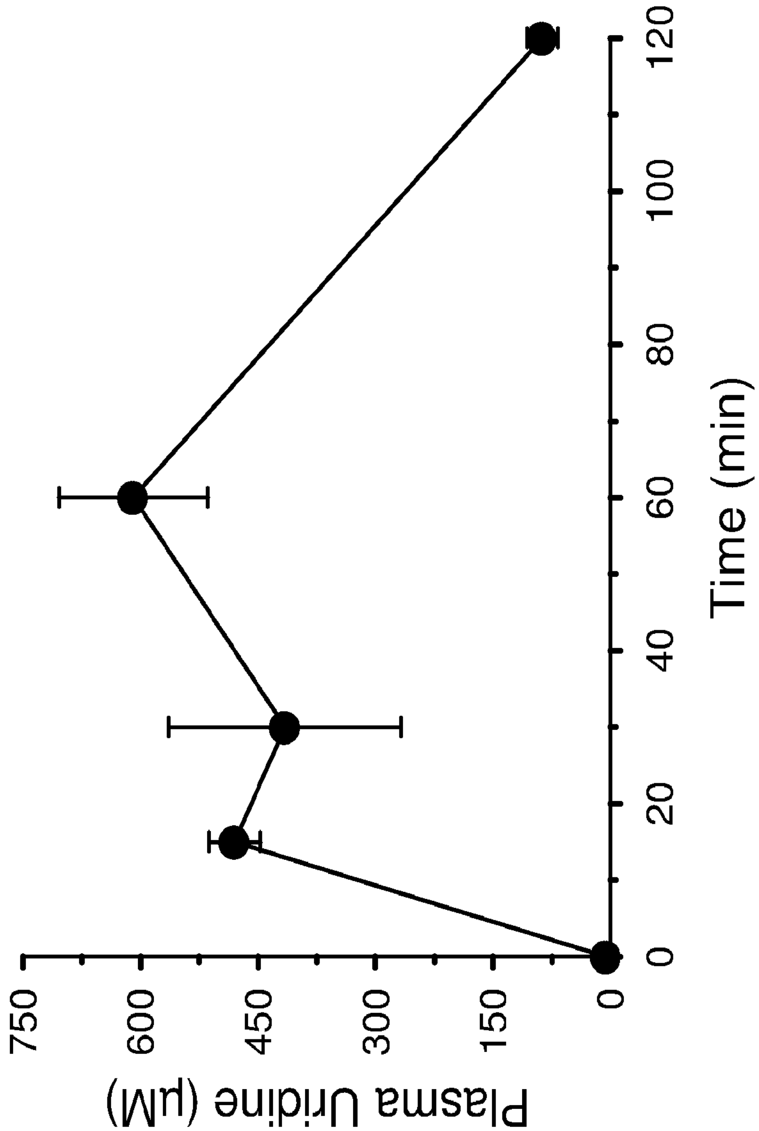

FIG. 4: Plasma uridine in mice after oral administration of AcAcDAU

AcAcDAU=5'-O-(acetoacetyl)-2',3'-di-O-acetyluridine

Figure 5:
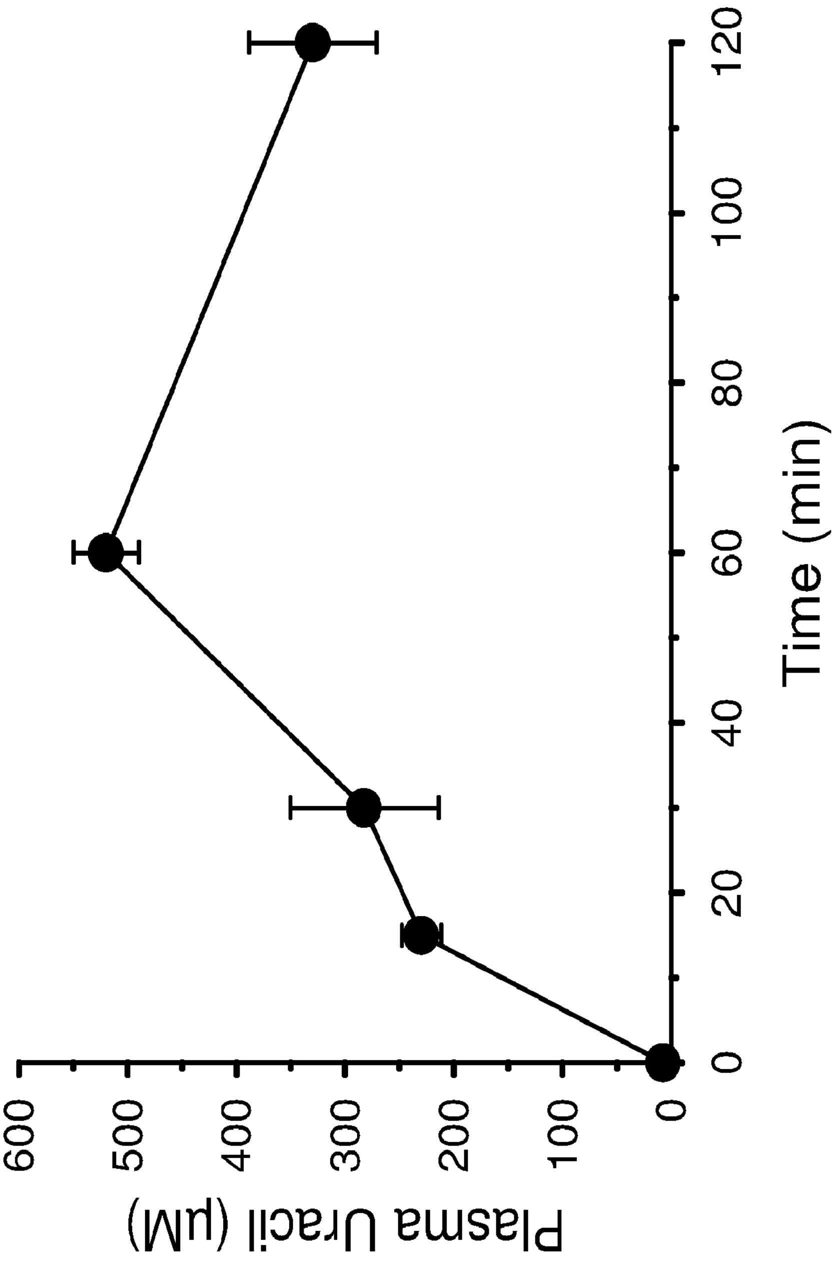

FIG. 5: Plasma uracil in mice after oral administration of AcAcDAU

AcAcDAU=5'-O-(acetoacetyl)-2',3'-di-O-acetyluridine

Figure 6:
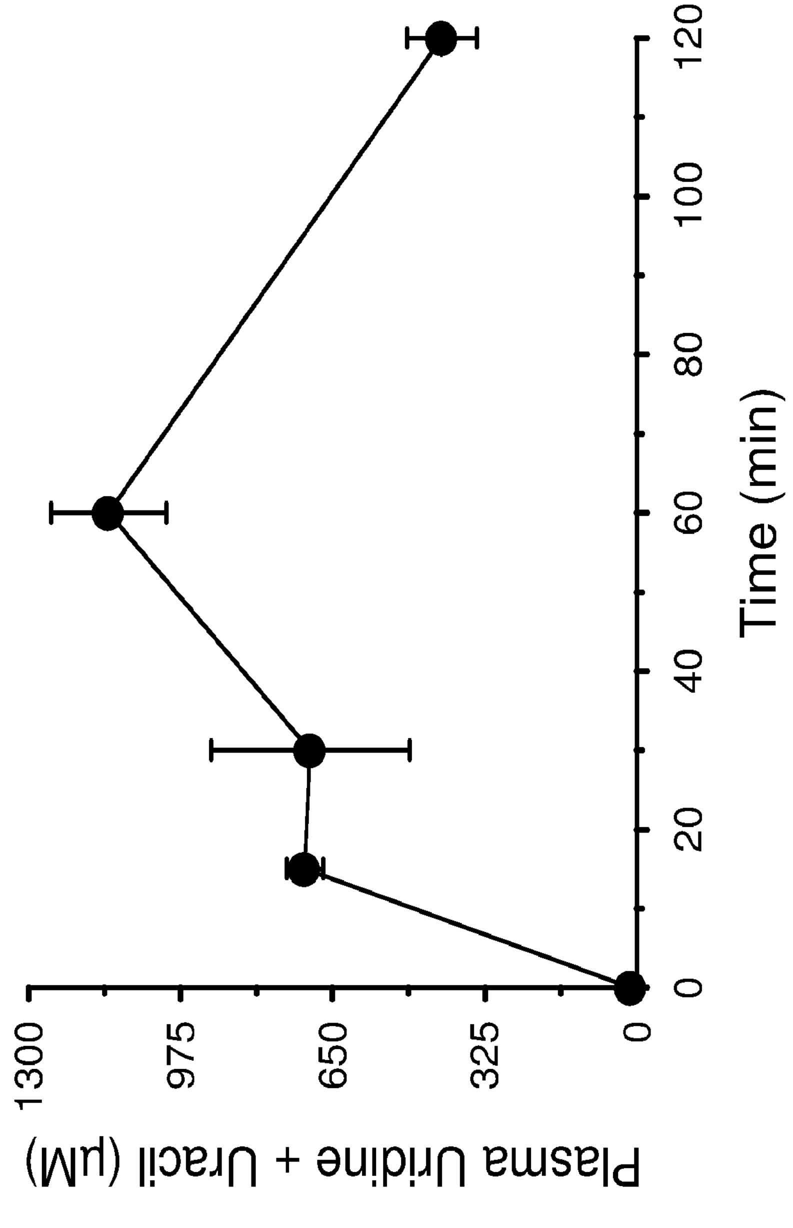

FIG. 6: Plasma uridine+uracil in mice after oral administration of AcAcDAU

AcAcDAU=5'-O-(acetoacetyl)-2',3'-di-O-acetyluridine

Figure 7:
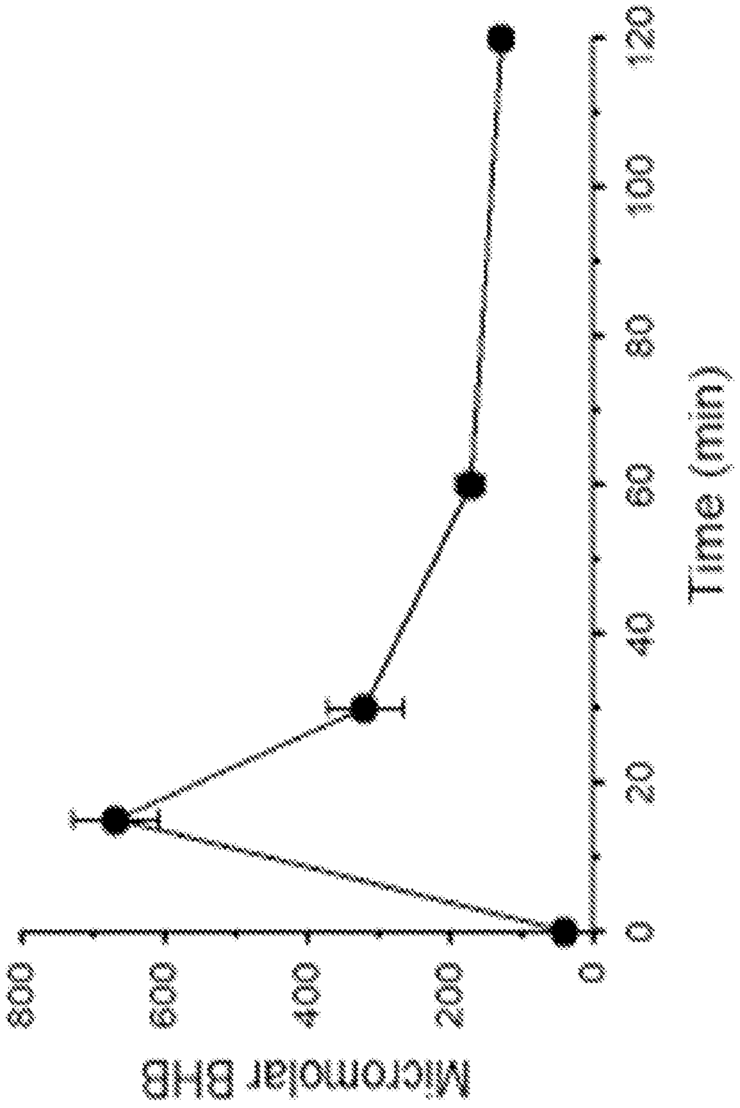

FIG. 7: Plasma beta-hydroxybutyrate in mice after oral administration of AcAcDAU BHB=Beta-hydroxybutyrate FIG. 8: Survival of mice receiving 60 mg/kg/day 3-nitropropionic acid and treated with oral uridine triacetate (UTA) 1000 mg/kg b.i.d. or 5'-O-acetoacetyl-2',3'-di-O-acetyluridine (AcAcDAU) 1113.5 mg/kg b.i.d.

DETAILED DESCRIPTION OF THE INVENTION

As used herein the transitional term "comprising" is open-ended. A claim utilizing this term can contain elements in addition to those recited in such claim. Thus, for example, the claims can read on treatment regimens that also include other therapeutic agents or therapeutic virus doses not specifically recited therein, as long as the recited elements or their equivalent are present.

ABBREVIATIONS

Certain chemical compounds are referred to herein by their chemical name or by the abbreviation or structural formula shown below. The compound AcAcDAU is within the scope of this invention.

UTA=uridine triacetate (2',3',5'-tri-O-acetyluridine)

Tri-AcAcU=2',3',5'-tri-O-(acetoacetyl)uridine, MW 496.42

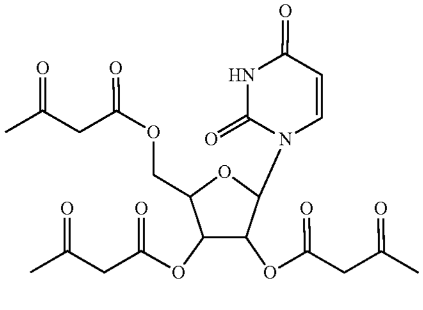 [SMILES: CC(=O)CC(=O)OCC1OC(n2ccc(=O)[nH]c2=O)C(OC(=O)CC(C)=O)C1OC(=O)CC(C)=O]

AcAcDAU=5'-O-(acetoacetyl)-2',3'-di-O-acetyluridine, MW 412.35

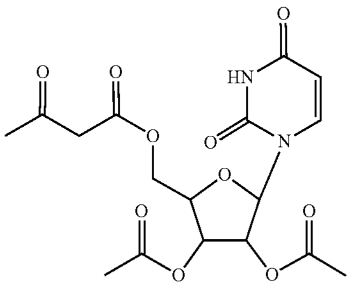 [SMILES: CC(=O)CC(=O)OCC1OC(n2ccc(=O)[nH]c2=O)C(OC(C)=O)C1OC(C)=O]

DA-HU 2' 3'-di-O-acetyl-5'-O-heptanoyluridine, MW 440.44

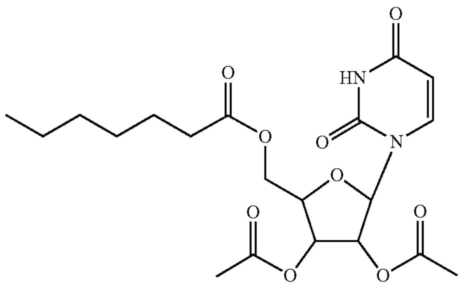 [SMILES: CCCCCCC(=O)OCC1OC(n2ccc(=O)[nH]c2=O)C(OC(C)=O)C1OC(C)=O]

DAU=2',3'-di-O-acetyluridine

AcAcU=5'-O-(acetoacetyl)uridine (also called 5'-O-Acetoacetyluridine)

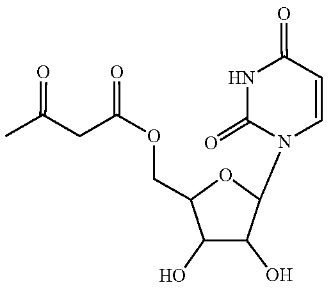 [SMILES: CC(=O)CC(=O)OCC1OC(n2ccc(=O)[nH]c2=O)C(O)C1O]

BHB=Beta-hydroxybutyrate (also called 3-hydroxybutyrate)

DCM=Dichloromethane (also called methylene chloride, chemical formula $CH_2Cl_2$)

DMF=Dimethylformamide, chemical formula $(CH_3)_2NC(O)H$

In accordance with the method, the compound for use, the use, and the pharmaceutical composition of this invention any conventional disorder characterized by cerebral metabolic energy failure or diminished mitochondrial energy reserve capacity in a mammalian subject can be treated or prevented. In one embodiment the disorder is a neurological disorder, for example a genetic neurodegenerative disease, an age-related neurodegenerative disorder, and a traumatic or ischemic brain injury. Examples of such genetic neurodegenerative diseases include, but are not limited to, Down Syndrome Dementia, Huntington's Disease, and Amyotrophic lateral sclerosis. Examples of such age-related neurodegenerative disorders include, but are not limited to, Parkinson's Disease, and senile dementia. The category of senile dementia includes, for example, Alzheimer's Disease and vascular dementia. Examples of such traumatic or ischemic brain injuries include, but are not limited to, secondary injury following traumatic brain injury, secondary injury following hypoxic-ischemic encephalopathy, secondary injury following birth asphyxia, secondary injury following ischemic stroke, secondary injury following hemorrhagic stroke, secondary injury following cardiac arrest, and secondary injury following drowning.

In another embodiment the disorder is a neuromuscular disorder. Examples of such neuromuscular disorders include, but are not limited to, age-related sarcopenia, muscle disuse atrophy, muscular dystrophy, myotonic dystrophy, chronic fatigue syndrome, and Friedreich's Ataxia.

In another embodiment the disorder is a heart failure. Examples of such heart failures include, but are not limited to dilated cardiomyopathy, right ventricular failure (including right ventricular failure secondary to pulmonary arterial hypertension), acute heart failure, and chronic heart failure.

In another embodiment the disorder is a primary genetic mitochondrial disease. Examples of such primary genetic mitochondrial diseases include, but are not limited to, MELAS (Mitochoncrial Encephalomyopathy with Lactic Acidemia and Stroke-like episodes), MERRF (Myoclonus, epilepsy, and myopathy with ragged red fibers), NARP (Neurogenic muscular weakness, ataxia, retinitis pigmentosa), NARP/MILS (Neurogenic muscular weakness, ataxia, retinitis pigmentosa/Maternally inherited Leigh syndrome), LHON (Lebers hereditary optic neuropathy) also known as "Mitochondrial blindness", KSS (Kearns-Sayre Syndrome), PMPS (Pearson Marrow-Pancreas Syndrome), PEO (Progressive external ophthalmoplegia), CPEO (Chronic progressive external ophthalmoplegia), Leigh Syndrome, MNGIE (Mitochondrial neurogastrointestinal encephalopathy syndrome), Alpers syndrome, Multiple mtDNA deletion syndrome, MtDNA depletion syndrome, Mitochondrial Complex I deficiency, Mitochondrial Complex II (SDH) deficiency, Mitochondrial Complex III deficiency, Mitochondrial Complex IV (Cytochrome c oxidase) deficiency, Mitochondrial Complex V deficiency, Adenine Nucleotide Translocator (ANT) deficiency, Pyruvate dehydrogenase (PDH) deficiency, Multiple mitochondrial DNA deletion syndromes, Barth syndrome, Mitochondrial myopathy, Mitochondrial epilepsy, and Mitochondrial renal tubular acidosis.

Additional examples of disorders that can be treated or prevented in accordance with this invention include: Ethylmalonic aciduria with lactic acidemia; 3-Methylglutaconic aciduria with acidemia; Refractory epilepsy with declines during infection; Asperger syndrome with declines during infection; Autism with declines during infection; Cerebral palsy with declines during infection; Dyslexia with declines during infection; Maternally inherited thrombocytopenia and leukemia syndrome; MARIAHS syndrome (Mitochondrial ataxia, recurrent infections, aphasia, hypouricemia/hypomyelination, seizures, and dicarboxylic aciduria); ND6 dystonia; Cyclic vomiting syndrome with declines during infection; 3-Hydroxyisobutyric aciduria with lactic acidemia; Diabetes mellitus with lactic acidemia; Uridine responsive neurologic syndrome (URNS); Familial Bilateral Striatal Necrosis (FBSN); Aminoglycoside-associated deafness; Splenic Lymphoma; Wolfram syndrome; Rental Tubular Acidosis/Diabetes/Ataxis syndrome; Lactic acidemia; Encephalomyopathy; 1+proteinuria; Aminoaciduria; Hydroxyprolinuria; Deficiency of cardiolipin; a neuromuscular degenerative disease; developmental delay in cognitive, motor, language, executive function or social skills;

epilepsy; peripheral neuropathy; optic neuropathy; autonomic neuropathy; neurogenic bowel dysfunction; sensorineural deafness; neurogenic bladder dysfunction; migraine; ataxia; renal tubular acidosis; dilating cardiomyopathy; steatohepatitis; hepatic failure, and lactic acidemia. Examples of developmental delay in cognitive, motor, language, executive function or social skills include, but are not limited to: pervasive developmental delay, Pervasive Developmental Delay-Not Otherwise Specified (PDD-NOS), Attention Deficit Hyperactivity Disorder (ADHD), Rett's Syndrome, and some forms of Autism.

In accordance with this invention the compound can be administered to any mammalian subject. In one embodiment the mammalian subject is a human subject. In accordance with this invention, any conventional route of administration can be utilized. Preferably the compound is administered orally. The skilled practitioner can titrate to optimize the dosage for a particular patient. Typically the compound is administered orally to a human patient in a dose of from one to three $g/m^2$ of body surface area. Usually the dose is administered two or three times per day.

It has been found that an acetoacetate substituent in the 5' position of the ribose moiety, combined with acetate substituents in the 2' and 3' positions yields a novel compound that delivers uridine into the circulation as well as or better than does uridine triacetate. The prodrug substituent is furthermore selected to provide additional or complementary therapeutic benefit, beyond facilitating uridine delivery.

In contrast, compounds such as uridine triacetoacetate (2',3',5'-tri-O-acetoacetyluridine; acetoacetate is one of the ketone bodies, an oxidized form of beta-hydroxybutyrate) or 5'-O-heptanoyl-2',3'-di-O-acetyl uridine provided relatively poor systemic uridine delivery after oral administration. Likewise, 5'-O-acetoacetyluridine delivered little uridine into the circulation, and 2',3'-di-O-acetyluridine delivered less than 30% as much uridine into the circulation versus an equimolar dose of uridine triacetate. In contrast, a hybrid combining structural moieties of these four relatively inactive molecules, 5'-O-acetoacetyl-2',3'-di-O-acetyluridine, delivered more uridine and uridine catabolites into the circulation than did an equimolar dose of uridine triacetate.

Acetoacetate, a ketone body with neuroprotective properties is also delivered concurrently with uridine when incorporated into 5'-O-(acetoacetyl)-2',3'-di-O-acetyluridine. Acetoacetate and beta-hydroxybutyrate, which are both delivered by oral administration of 5'-O-(acetoacetyl)-2',3'-di-O-acetyluridine are problematic to deliver orally, in part due to an unpalatable taste, such that ester prodrugs of these ketone bodies have been proposed, notably 3-hydroxybutyl 3-hydroxybutyrate enantiomerically enriched with respect to the (3R, 3R') enantiomer (the R [or D] enantiomer is the natural form in mammalian biochemistry, whereas chemical synthesis of BHB initially results in a racemic mixture of enantiomers). 5'-O-(acetoacetyl)-2',3'-di-O-acetyluridine overcomes the palatability problem of the free keto acids and initially delivers acetoacetate cleaved from the uridine scaffold, which converts in vivo to R-BHB without the need for enantiomeric enrichment during chemical synthesis and purification. A single agent with dual, complementary pharmacological activities is also advantageous from the perspective of regulatory issues involving clinical trial complexity for combination drugs, and for reducing burdens on patients that may limit compliance.

Conversion of acetoacetate to BHB via the enzyme beta-hydroxybutyrate dehydrogenase uses NADH as an electron donor, resulting in regeneration of NAD+. In some disease states associated with mitochondrial respiratory chain dysfunction, a high NADH/NAD+ ratio, due to limited capacity of the respiratory chain to accept electrons from NADH, results in important secondary pathology, as NADH/NAD+ ratios affect activity of a large number of cytosolic enzymes. Maintenance of an excessive NADH/NAD+ ratio is termed "reductive stress", and is a recognized contributor to tissue dysfunction and adverse effects on lifespan in disorders with impaired mitochondrial electron transport chain deficits. Administration of exogenous AcAcDAU results in net oxidation of NADH to yield NAD+, generating BHB, which itself has important pharmacological and physiological benefits, both as an alternative fuel for the brain and other tissues, and as a signaling molecule, with known anti-inflammatory, antiepileptic and other effects. Therefore, AcAcDAU is useful for relieving reductive stress in disorders characterized by NADH accumulation secondary to electron transport chain dysfunction, with NADH oxidation by acetoacetate complementing the improvement of mitochondrial bioenergetic efficiency mediated by the uridine moiety. In addition, BHB is known to have pleiotropic potential benefits, not necessarily mediated by relief of reductive stress, at concentrations achieved after oral administration of AcAcDAU, including but not anti-inflammatory and anti-seizure activity.

In an embodiment of the method for producing 5'-O-Acetoacetyl-2',3'-di-O-acetyluridine described above, step (a) is performed at a temperature of from 90° C. to 110° C., for example at a temperature of about 110° C. In another embodiment step (b) is performed at a temperature of from room temperature to 75° C., for example at a temperature of about 65° C. In another embodiment step (c) is performed at about room temperature. Room temperature is typically about 25° C. Preferably the method of for producing 5'-O-Acetoacetyl-2',3'-di-O-acetyluridine described above further comprises as step (e), purifying the crude 5'-O-Acetoacetyl-2',3'-di-O-acetyluridine from step (d) to yield purified 5'-O-Acetoacetyl-2',3'-di-O-acetyluridine.

The invention will be better understood by reference to the following examples, which illustrate but do not limit the invention described herein.

EXAMPLES

Example 1: Synthesis of 5'-O-(acetoacetyl)-2',3'-di-O-acetyluridine, 5'-O-(acetoacetyl)-2'-O-acetyl-3'-O-formyluridine, and 5'-O-(acetoacetyl)-3'-O-acetyl-2'-O-formyluridine

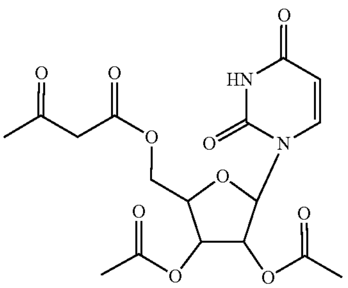

-continued

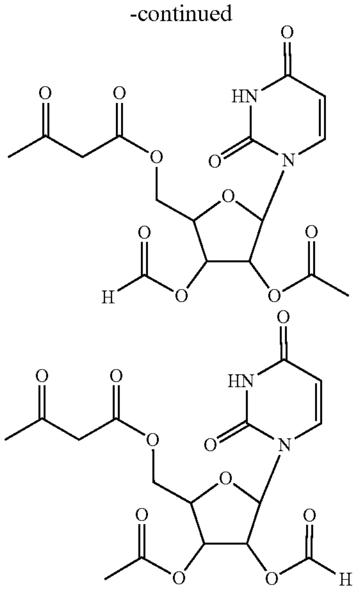

A mixture of 2',3'-O-isopropylideneuridine (5.21 g, 18.3 mmol) and 25 mL of N-methylpyrrolidinone was heated to 110° C., and then 2,2,6-trimethyl-4H-1,3-dioxin-4-one (3.00 mL, 22.6 mmol). After 2 hr, the mixture was cooled and partitioned between ethyl acetate (3×100 mL) and water (2×100 mL). The organic phases were washed with brine (100 mL), dried over anhydrous $MgSO_4$, and concentrated in vacuo to give a dark brown oil. Rf 0.50 (10% MeOH/DCM). The crude mixture was heated at 65° C. in a mixture of 20 mL of formic acid and 20 mL of water for 4 hr. Then, the volatile components were evaporated in vacuo. Rf 0.29 (10% MeOH/DCM).

A mixture of the crude reaction product and 6 mL of pyridine and 36 mL of DCM was cooled by an ice bath. Then, acetyl chloride (3.00 mL, 42.0 mmol) was added slowly. After 2 hr, 5 mL of water were added and the mixture was concentrated. The residue was taken up in ethyl acetate (100 mL) washed successively by 100 mL of water, saturated sodium bicarbonate, water, 1M HCl, and water. The aqueous phases were extracted with ethyl acetate (2×100 mL). The organic phases were washed with brine (100 mL), dried over anhydrous $MgSO_4$, and concentrated in vacuo. Purification of the major product by flash chromatography using a step gradient of 1%, 2%, and 3% MeOH/DCM gave 1.6 g of pale yellow material. Rf 0.24 (5% MeOH/DCM) Analysis by LC/MS showed that the material was a 9.4:1 mixture of 5'-O-(acetoacetyl)-2',3'-di-O-acetyluridine and a combination of 5'-O-(acetoacetyl)-2'-O-acetyl-3'-O-formyluridine and 5'-O-(acetoacetyl)-3'-O-acetyl-2'-O-formyluridine.

Scheme 1

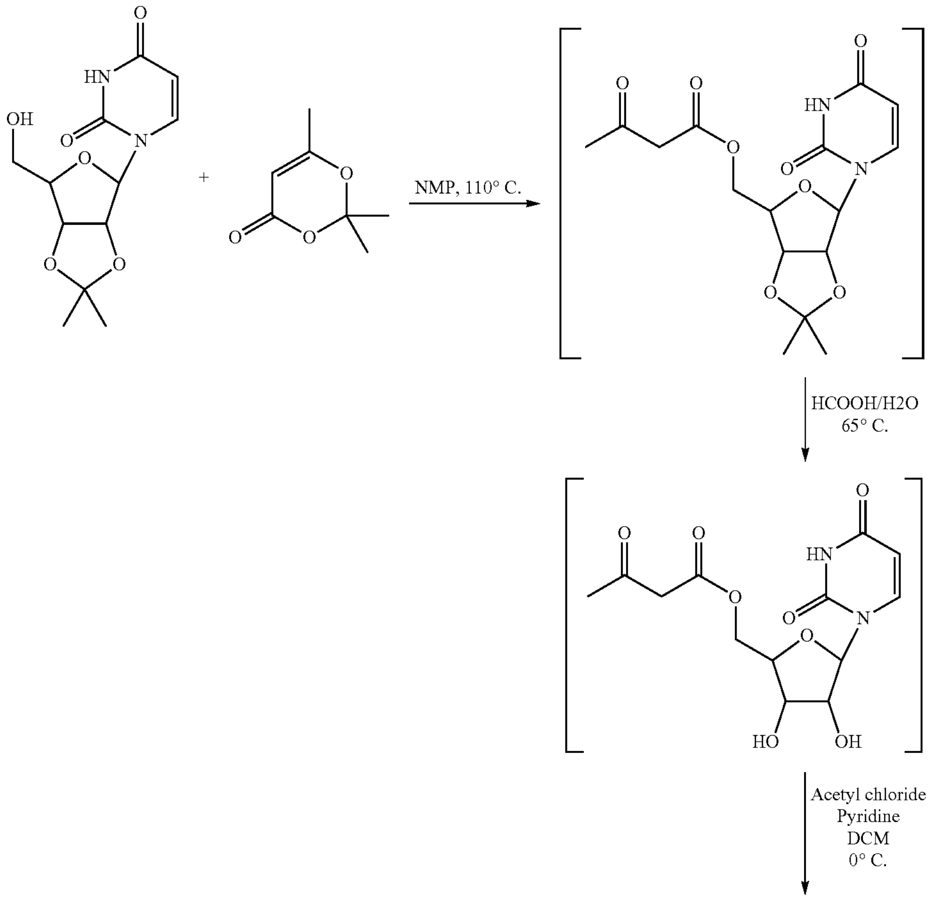

-continued

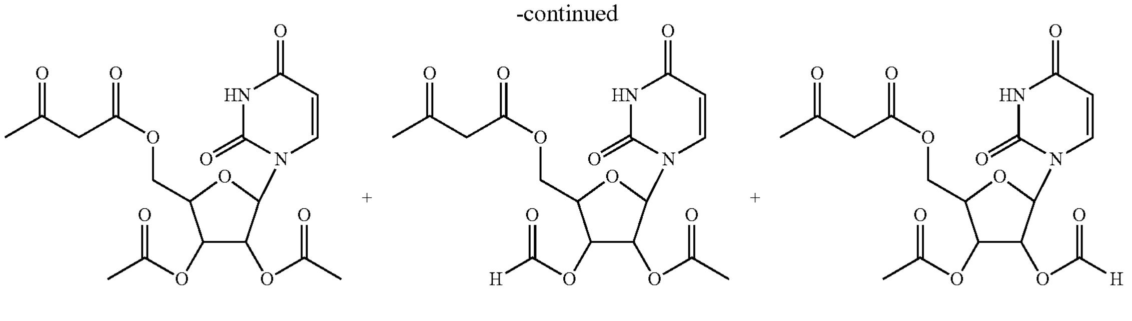

Example 2: Improved Synthesis of 5'-O-acetoacetyl-2',3'-di-O-acetyluridine

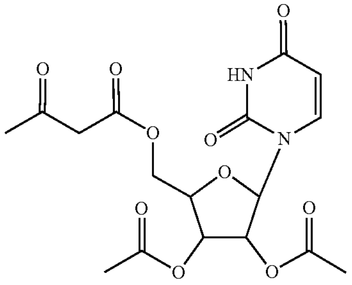 [SMILES: CC(=O)CC(=O)OCC1OC(n2ccc(=O)[nH]c2=O)C(OC(C)=O)C1OC(C)=O]

5'-O-Acetoacetyl-2',3'-O-isopropylideneuridine

A mixture of 2',3'-O-isopropylideneuridine (40 g, 141 mmol) and 2,2,6-trimethyl-4H-1,3-dioxin-4-one (18.7 mL, 141 mmol) in 60 mL of DMF was heated at 110° C. for 2 hr. Then the mixture was cooled and the volatile components were evaporated. The residue was partitioned between ethyl acetate and water, and the organic phases were washed with brine, dried over anhydrous $MgSO_4$, and concentrated by evaporation. Purification by flash chromatography (3% MeOH/DCM) gave the product contaminated by colored material. Partial decolorization by 2 g activated charcoal in ethyl acetate gave 35 g of product as a light brown colored syrup. Rf 0.71 (10% MeOH/DCM).

5'-O-Acetoacetyluridine

A mixture of 5'-O-acetoacetyl-2',3'-O-isopropylideneuridine (35 g, 95 mmol), 100 mL of acetic acid, and 100 mL of water was heated at 65° C. for 24 hr., at which time TLC of an aliquot of the mixture showed that starting material was nearly consumed. The volatile components were evaporated in vacuo. The crude product was carried on. Rf 0.32 (10% MeOH/DCM).

5'-O-Acetoacetyl-2',3'-di-O-acetyluridine

The crude product obtained above was taken up in 100 mL of DCM and 30 mL of pyridine, and then the solvents were evaporated in vacuo. The residue was taken up in 250 mL of DCM and 19 mL of pyridine. Once the mixture was homogeneous, 22 mL of acetic anhydride was added. The mixture was stirred for 3 days. Then, the solvent was switched to 500 mL of ethyl acetate, and neutralized with saturated $NaHCO_3$. The volatile components were evaporated to remove excess pyridine. The residue was partitioned between ethyl acetate and water, 1 M HCl, water, and brine, and the organic phases were dried over anhydrous $MgSO_4$ and concentrated in vacuo. Purification by flash chromatography (3% MeOH/DCM) gave 25.7 g of product as a white foamy solid. $^1H$ NMR (400 MHz, $CDCl_3$) δ 9.04 (br s, 1H), 7.47 (d, 1H, J=8 Hz), 6.07 (d, 1H, J=6 Hz), 5.84 (d, 1H, J=8 Hz), 5.38-5.35 (m, 1H), 5.31-5.28 (m, 1H), 4.90 (ABX, 1H, J=2.5, 12.5 Hz), 4.39 (ABX, 1H, J=3.7, 12.4 Hz), 4.35-4.32 (m, 1H), 3.61 (AB, 1H, J=16 Hz), 3.56 (AB, 1H, J=16 Hz), 2.97 (s, 3H), 2.14 (s, 3H), 2.10 (s, 3H); LC/MS 99.4% purity (260 nm); MW: Calc. 412, Found 412; Rf 0.24 (5% MeOH/DCM).

Scheme 2

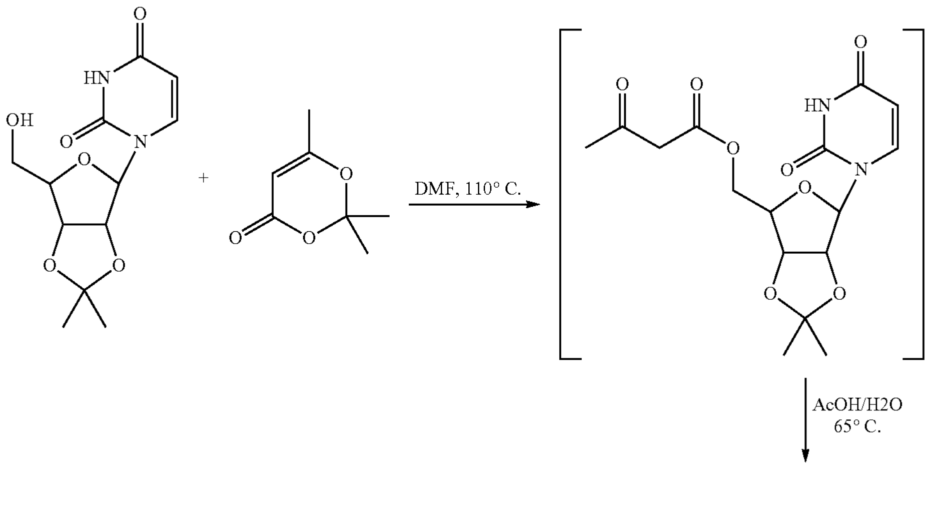

-continued

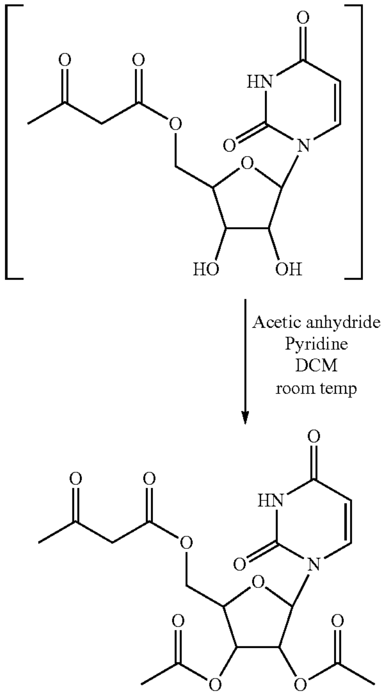

Example 3: Improved Synthesis of 5'-O-Acetoacetyluridine

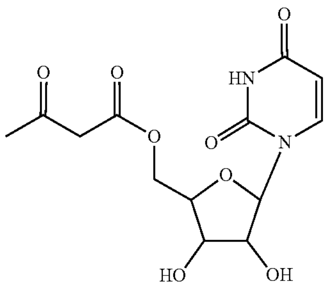 [SMILES: CC(=O)CC(=O)OCC1OC(n2ccc(=O)[nH]c2=O)C(O)C1O]

5'-O-Acetoacetyluridine

A mixture of 5'-O-acetoacetyl-2',3'-O-isopropylideneuridine (11.4 g, 31.0 mmol), 75 mL of acetic acid, and 75 mL of water was heated at 65° C. for 24 hr., at which time TLC of an aliquot of the mixture showed that starting material was nearly consumed. The volatile components were evaporated in vacuo. The residue was purified by flash chromatography (step gradient of 5% and 7% MeOH/DCM) to give 6.10 g of the product as a white foamy solid. $^{1}H$ NMR (400 MHz, DMSO-$d_6$) δ 11.36 (s, 1H), 7.59 (d, 1H, J=8 Hz), 5.76 (d, 1H, J=5 Hz), 5.64 (d, 1H, J=8 Hz), 5.46 (d, 1H, J=6 Hz), 5.29 (d, 1H, J=6 Hz), 4.31 (1H, ABX, J=3, 12 Hz), 4.22 (1H, ABX, J=5, 12 Hz), 4.07 (q, 1H, J=5 Hz), 4.02-3.98 (m, 1H), 3.95 (q, 1H, J=5 Hz), 3.68 (2H, AB), 2.19 (s, 3H); $^{13}C$ NMR (100 MHz, DMSO-$d_6$) δ 201.63, 167.07, 163.01, 150.62, 140.75, 101.99, 88.48, 81.04, 72.63, 69.68, 64.26, 49.46, 30.10; Rf 0.32 (10% MeOH/DCM).

Example 4: Plasma Uridine and [Uridine+Uracil] in Mice after Oral Administration of Uridine Prodrugs Chemical(s): HPMC (Hydroxypropyl)methyl cellulose (SIGMA-Aldrich: cat #H3785, CAS 9004-65-3); uridine triacetate (2',3',5'-tri-O-acetyluridine): UTA, Item Code D000156, Lot #Q000001095, made by Almac Sciences; 2',3',5'-tri-O-(acetoacetyl)uridine: Tri-AcAcU; 5'-O-(acetoacetyl)-2',3'-di-O-acetyluridine: AcAcDAU; 2',3'-di-O-acetyl-5'-O-heptanoyluridine: DA-HU. (Note: the AcAcDAU used in this experiment was the mixture of 9.4 parts 5'-O-(acetoacetyl)-2',3'-di-O-acetyluridine and 1 part a combination of 5'-O-(acetoacetyl)-2'-O-acetyl-3'-O-formyluridine and 5'-O-(acetoacetyl)-3'-O-acetyl-2'-O-formyluridine from Example 1 above.)

Vehicle: Aqueous HPMC was used as a vehicle for oral administration of the uridine derivatives.

Dosing Formulation: UTA and other uridine derivatives were prepared in 0.75% HPMC. UTA and other uridine derivatives were added to 0.75% HPMC and homogenized to eliminate clumps. The suspension were made up to the desired volume and concentration and sonicated to disaggregate any small leftover clumps into fine particles. Suspensions were stored at 4° C. until use. Suspensions were used within 24 hrs of preparation.

Dosing: Mice received a dose of 600 mg/Kg UTA gavaged at 0.02 ml/g body weight. Other uridine derivatives were dosed in the same manner at concentrations containing amounts of uridine equimolar to UTA.

Animals: Female CD-1 mice.

| Species | Strains | Gender | Number | Age and Weight Range at Shipment | Vendor | Diet and Housing |
|---|---|---|---|---|---|---|
| Mouse | CD-1 | Females | 39 | ~26-30 g | Envigo | Harlan Teklad |

-continued

| Species | Strains | Gender | Number | Age and Weight Range at Shipment | Vendor | Diet and Housing |
|---|---|---|---|---|---|---|
| | | | | | | 2016, ad libitum, housed 5/cage |

The general initial layout for the experiment involved gavaging groups of 6 mice with uridine derivatives and obtaining blood samples at several times points thereafter (3 mice were bled for 2 time points (15 and 60 minutes), and another 3 mice were bled for the other 2 time points (30 and 120 minutes). Each experiment included an HPMC (vehicle only) time point with 3 mice to establish a baseline for blood uridine.

| Group No. | No. of Animals | Bleeding Time After Dosing |
|---|---|---|
| UTA | 6 | 15, 30, 60, & 120 min |
| Tri-AcAcU | 6 | 15, 30, 60, & 120 min |
| AcAcDAU | 6 | 15, 30, 60, & 120 min |
| DA-HU | 6 | 15, 30, 60, & 120 min |
| HPMC | 3 | — |

Blood samples were collected into plasma separation tubes, which were centrifuged immediately after blood collection, and aliquots of plasma were frozen for subsequent processing. Plasma was later deproteinated, and uridine and uracil were quantified by liquid chromatography using UV absorbance detection and mass spectrometry.

Delivery of uridine into the bloodstream was assessed by monitoring plasma uridine and the sum of uridine and uracil [uridine+uracil], as uracil is the first product in enzymatic degradation of uridine. Mice convert administered uridine to uracil more rapidly and extensively than do humans.

Of the compounds tested, oral administration of 5'-O-(acetoacetyl)-2',3'-di-O-acetyluridine (AcAcDAU) resulted in delivery of systemic uridine and [uridine+uracil to a degree similar to or greater than did oral delivery of uridine triacetate.

Figure 1:
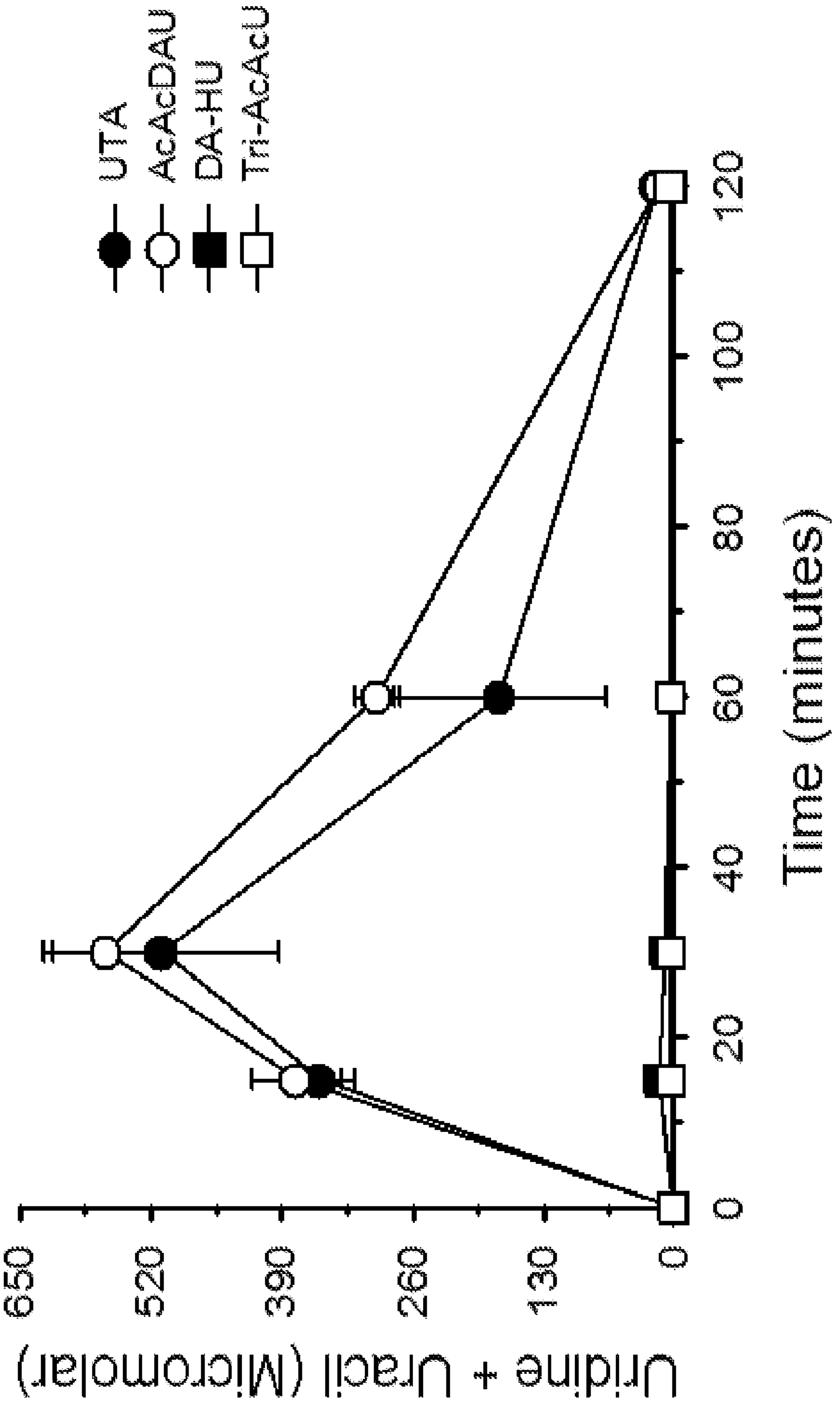
FIG. 1: Plasma [uridine+uracil] in mice after oral administration of uridine prodrugs UTA=uridine triacetate (2',3',5'-tri-O-acetyluridine)
Figure 3:
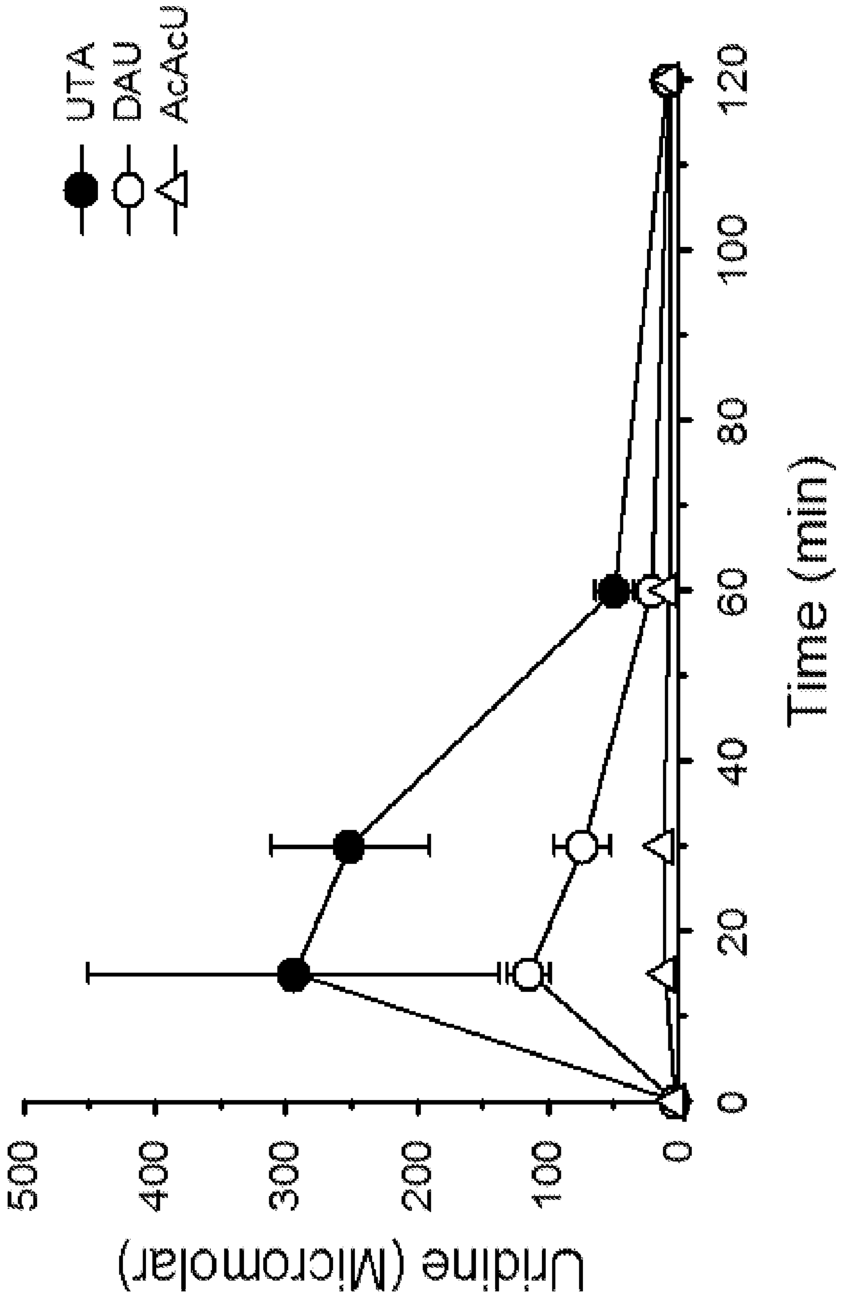

Plasma [uridine+uracil] concentrations and plasma uridine after administration of a set of uridine prodrugs are shown in FIGS. 1 and 2. FIG. 3 shows plasma uridine in mice after oral administration of a different set of uridine prodrugs.

Example 5: Plasma uridine and beta-hydroxybutyrate in mice after oral administration of 5'-O-(acetoacetyl)-2',3'-di-O-acetyluridine An important feature of 5'-O-(acetoacetyl)-2',3'-di-O-acetyluridine (AcAcDAU) is that it yields simultaneous or concurrent delivery of both uridine and acetoacetate via a single drug molecule. Acetoacetate in plasma is in equilibrium with beta-hydroxybutyrate (BHB) mirroring free NADH/NAD+ ratios in hepatic mitochondria, and heavily favoring BHB as the more prevalent of the two ketone bodies under normal physiological conditions. Moreover, BHB is stable after blood sampling and processing, whereas acetoacetate is labile. Therefore, plasma BHB was measured along with plasma uridine in mice receiving oral AcAcDAU.

Chemical(s): HPMC (Hydroxypropyl) methyl cellulose (SIGMA-Aldrich: cat #H3785, CAS 9004-65-3), 5'-O-(acetoacetyl)-2',3'-di-O-acetyluridine (AcAcDAU; lot #432168B). This experiment used the AcAcDAU from Example 2.

Vehicle: Aqueous HPMC was used as a vehicle for oral administration of the uridine derivatives.

Dosing Formulation: UTA and other uridine derivatives were prepared in 0.75% HPMC. AcAcDAU was added to 0.75% HPMC and homogenized to eliminate clumps. The suspensions were made up to the desired volume and concentration and sonicated to disaggregate any small left-over clumps into fine particles. Suspensions were stored at 4° C. until use. Suspensions were used within 24 hrs of preparation.

Dosing: Mice received a dose of 2350 mg/Kg AcAcDAU gavaged at 0.02 ml/g body weight. Control mice received only the 0.75% HPMC vehicle Animals: Female CD-1 mice.

| Species | Strain | Gender | Number | Age and Weight Range at Shipment | Vendor | Diet and Housing |
|---|---|---|---|---|---|---|
| Mouse | CD-1 | Females | 10 | DOB May 22, 2020 | Envigo | Harlan Teklad 2016, ad libitum, housed 5/cage |

General Experimental Design: The general layout for the experiment involved gavaging mice with AcAcDAU and obtaining blood samples at several time points thereafter (see table below for details). The experiment included a group with 2 mice gavaged with HPMC only and bled at 60 and 120 min for determination of baseline plasma uridine.

| Gavage | Animals | Bleeding Time After Dosting |
|---|---|---|
| AcAcDAU | A1, A2, A3, A4 | 15 and 60 min |
| AcAcDAU | A5, A6, A7, A8 | 30 and 120 min |
| HPMC | C1, C2 | 60 and 120 min |

Mice received 0.02 ml/g bodyweight of a suspension (0.75% hydroxypropylmethylcellulose in water) with a concentration of AcAcDAU of 117 mg/ml for a dose of 2,350 mg/Kg body weight. At each time point, (15, 30, 60 and 120 minutes post administration), blood samples (~100 microliters) from 4 mice were collected into plasma separator tubes. Samples were rapidly centrifuged and the resultant plasma was frozen on dry ice. Subsequently, the plasma samples were deproteinized and subjected to reverse-phase HPLC analysis for measurement of plasma uridine and its initial metabolite uracil. Aliquots of the same plasma samples were also used for measurement of BHB concentrations with a commercial enzymatic assay kit.

Plasma uridine and its initial metabolite uracil were elevated after oral administration of AcAcDAU, as shown in FIGS. 4, 5 and 6. Plasma beta-hydroxybutyrate was also elevated by administration of AcAcDAU, as shown in FIG. 7, with an Area-Under-the Curve (AUC) of 24,212 nmol/ml×min.

Example 6: Protection Against Mortality Caused by 3-nitropropionic acid by 5'-acetoacetyl-2',3'-di-O-acetyluridine and 2'3'5'-tri-O-acetyluridine 5'-O-acetoacetyl-2',3'-di-O-acetyluridine (AcAcDAU) delivers both uridine and acetoacetate (and beta-hydroxybutyrate [BHB] derived from acetoacetate) into the circulation after oral administration. A study was designed to compare relative efficacy of UTA versus AcAcDAU in a model of progressive lethal mitochondrial energy failure. Mitochondrial dysfunction was produced by daily administration of 3-nitropropionic acid (3-NP; 60 mg/kg/day) by intraperitoneal injection. 3-NP is an irreversible inhibitor of succinate dehydrogenase (Complex II of the mitochondrial electron transport chain). Daily dosing with 3-NP results in progressive diminution of mitochondrial capacity to maintain ATP production, eventually resulting in mortality from both neurodegeneration and cardiomyopathy.

Female CD-1 mice at approximately 16 weeks of age were divided into weight-matched groups of 10 mice each. All mice received daily intraperitoneal injections of 3-NP (60 mg/kg) in a volume of 0.01 ml per gram of body weight.

In addition to daily injections of 3-NP, the three groups of mice received 1) Vehicle; 2) UTA; or 3) AcAcDAU. This experiment used the AcAcDAU from Example 2. These treatments were administered orally, by gavage, in a volume of 0.02 ml per gram of body weight.

Groups:

1. Vehicle Control (0.75% HPMC; hydroxypropylmethylcellulose)
2. Uridine triacetate 1000 mg/kg BID (suspended in 0.75% HPMC)
3. AcAcDAU 1113.5 mg/kg (molar equivalent to 1000 mg/kg UTA) BID (dissolved in 0.75% HPMC)

The treatment schedule was as follows:

| Group | 7:00 AM Gavage | 4:00 PM Gavage | 5:00 PM ip injection |
|---|---|---|---|
| 1 | HPMC | HPMC | 3-NP (60 mg/Kg) |
| 2 | UTA | UTA | 3-NP (60 mg/Kg) |
| 3 | AcAcDAU | AcAcDAU | 3-NP (60 mg/Kg) |

Body weights were recorded each day to adjust drug doses as mice lost weight during repeated treatment with 3-NP.

Survival times (median survival; the time point at which 50% of animals in a group had died) and percent survival at the end of the 11 day study were used to quantify and compare protective effects of the test agents.

Figure 8:
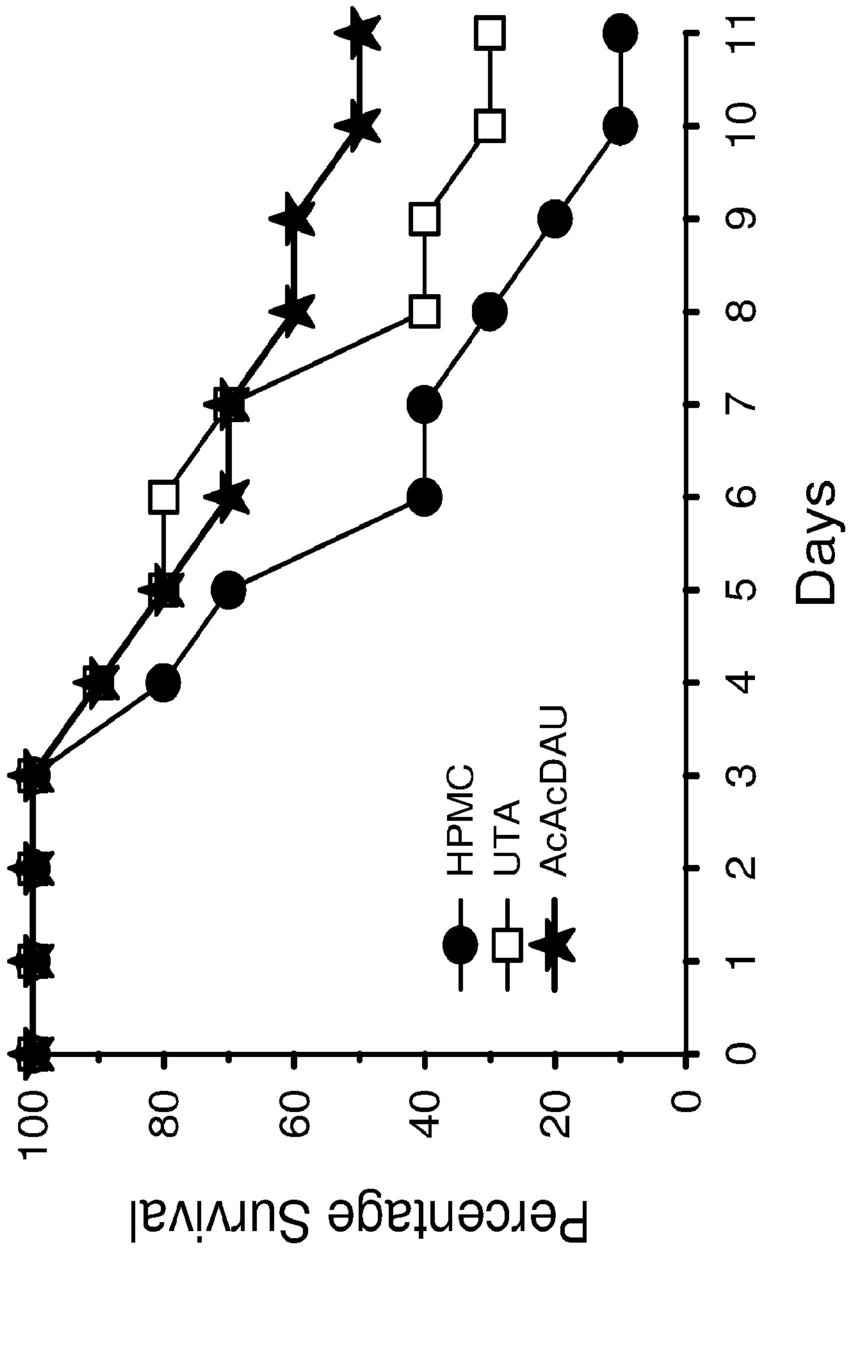

Results:

The final survival percentages and median survival times at the end of the study are shown in the following Table 1 and in FIG. 8.

TABLE 1

Survival of mice receiving 60 mg/kg/day 3-nitropropionic acid and treated with oral uridine triacetate (UTA) 1000 mg/kg b.i.d. or 5'-acetoacetyl-2',3'-di-O-acetyluridine (AcAcDAU) 1113.5 mg/kg b.i.d.

| Group | % Survival | Median Survival |
|---|---|---|
| Vehicle Control | 10% (1/10) | 5.5 Days |
| UTA | 30% (5/10) | 7 Days |
| AcACDAU | 50% (2/10) | >11 Days |

Equimolar doses of UTA and AcAcDAU both improved survival time during progressive mitochondrial failure versus vehicle alone. AcAcDAU treatment displayed a longer median survival time than did administration of UTA in mice subjected to progressive mitochondrial energy failure.

Example 7: Protection Against Mortality Due to 3-nitropropionic acid by 5'-acetoacetyl-2',3'-di-O-acetyluridine and 2'3'5'-tri-O-acetyluridine Example 6 showed that AcAcDAU treatment resulted in better survival in a model of lethal progressive mitochondrial failure effects when administered orally at 1113.5 mg/kg per dose versus the molar equivalent of UTA (1000 mg/kg/dose). In this example the effect of higher doses of UTA (2000 mg/kg/dose) versus equimolar AcAcDAU (2227 mg/kg/dose) were compared in the same model system.

Groups:

1. Vehicle Control (0.75% HPMC; hydroxypropylmethylcellulose)
2. Uridine triacetate 2000 mg/kg BID (suspended in 0.75% HPMC)

AcAcDAU 2227 mg/kg (molar equivalent to 2000 mg/kg UTA) BID (dissolved in 0.75% HPMC). This experiment used the AcAcDAU from Example 2. The treatment schedule was as follows:

| Group | 7:00 AM Gavage | 4:00 PM Gavage | 5:00 PM ip injection |
|---|---|---|---|
| 1 | HPMC | HPMC | 3-NP (60 mg/Kg) |
| 2 | UTA | UTA | 3-NP (60 mg/Kg) |
| 3 | AcAcDAU | AcAcDAU | 3-NP (60 mg/Kg) |

Body weights were recorded each day to adjust drug doses as mice lost weight during repeated treatment with 3-NP.

Percent survival of mice in each group of 10 mice at the end of the 10 day study were used to quantify and compare protective effects of the test agents.

Results:

The final survival percentages at the end of the study are shown in the following Table 2.

Table 2: Survival of mice receiving 60 mg/kg/day 3-nitropropionic acid and treated with oral uridine triacetate (UTA) 2000 mg/kg b.i.d. or 5'-acetoacetyl-2',3'-di-O-acetyluridine (AcAcDAU) 2227 mg/kg b.i.d.

| Group | % Survival |
|---|---|
| Vehicle Control | 30% (3/10) |
| UTA | 70% (7/10) |
| AcAcDAU | 100% (10/10) |

UTA and AcAcDAU both improved survival time during progressive mitochondrial failure versus vehicle alone. AcAcDAU treatment resulted in better survival at the 10 day time point than did administration of equimolar doses of oral UTA in mice subjected to progressive mitochondrial energy failure.

What is claimed is:

1. A compound, 5'-O-(Acetoacetyl)-2',3'-di-O-acetyluridine.

2. A method of treating a disorder characterized by cerebral metabolic energy failure or diminished mitochondrial energy reserve capacity in a mammalian subject, comprising administering to the subject an amount of the compound of claim 1 effective to treat the disorder, wherein the disorder is:

(i) a neurological disorder;

(ii) a neuromuscular disorder;

(iii) a heart failure; or (iv) a primary genetic mitochondrial disease.

3. The method of claim 2, wherein the disorder is a neurological disorder.

4. The method of claim 3, wherein the neurological disorder is selected from the group consisting of a genetic neurodegenerative disease, an age-related neurodegenerative disorder, and a traumatic or ischemic brain injury.

5. The method of claim 4, wherein the neurological disorder is a genetic neurodegenerative disease.

6. The method of claim 5, wherein the genetic neurodegenerative disease is selected from the group consisting of:

Down Syndrome Dementia,

Huntington's Disease, and

Amyotrophic lateral sclerosis.

7. The method of claim 4, wherein the neurological disorder is an age-related neurodegenerative disorder.

8. The method of claim 7, wherein the age-related neurodegenerative disorder is selected from the group consisting of:

Parkinson's Disease, and senile dementia.

9. The method of claim 8, wherein the senile dementia is selected from the group consisting of Alzheimer's Disease and vascular dementia.

10. The method of claim 4, wherein the neurological disorder is a traumatic or ischemic brain injury.

11. The method of claim 10, wherein the traumatic or ischemic brain injury is selected from the group consisting of:

secondary injury following traumatic brain injury, secondary injury following hypoxic-ischemic encephalopathy, secondary injury following birth asphyxia secondary injury following ischemic stroke, secondary injury following hemorrhagic stroke, secondary injury following cardiac arrest, and secondary injury following drowning.

12. The method of claim 2, wherein the disorder is a neuromuscular disorder.

13. The method of claim 12, wherein the neuromuscular disorder is selected from the group consisting of:

age-related sarcopenia,

Muscle disuse atrophy, muscular dystrophy, myotonic dystrophy, chronic fatigue syndrome, and Friedreich's Ataxia.

14. The method of claim 2, wherein the disorder is a heart failure.

15. The method of claim 14, wherein the heart failure is selected from the group consisting of:

dilated cardiomyopathy, right ventricular failure, acute heart failure, and chronic heart failure.

16. The method of claim 2, wherein the disorder is a primary genetic mitochondrial disease.

17. The method of claim 16, wherein the primary genetic mitochondrial disease is selected from the group consisting of:

MELAS (Mitochoncrial Encephalomyopathy with Lactic Acidemia and stroke-like episodes), MERRF (Myoclonus, epilepsy, and myopathy with ragged red fibers),

NARP,

NARP/MILS (Neurogenic muscular weakness, ataxia, retinitis pigmentosa/Maternally inherited Leigh syndrome), LHON (Lebers hereditary optic neuropathy) "Mitochondrial blindness", KSS (Kearns-Sayre Syndrome), PMPS (Pearson Marrow-Pancreas Syndrome), PEO (Progressive external ophthalmoplegia), CPEO (Chronic progressive external ophthalmoplegia), Leigh Syndrome, MNGIE (Mitochondrial neurogastrointestinal encephalopathy syndrome), Alpers syndrome, Multiple mtDNA deletion syndrome, MtDNA depletion syndrome, Mitochondrial Complex I deficiency, Mitochondrial Complex II (SDH) deficiency, Mitochondrial Complex III deficiency, Mitochondrial Complex IV (Cytochrome c oxidase) deficiency, Mitochondrial Complex V deficiency, Adenine Nucleotide Translocator (ANT) deficiency, Pyruvate dehydrogenase (PDH) deficiency, Multiple mitochondrial DNA deletion syndromes, Barth syndrome, Mitochondrial myopathy, Mitochondrial epilepsy, and Mitochondrial renal tubular acidosis.

18. The method of claim 2, wherein the mammalian subject is a human subject.

19. The method of claim 2, wherein the compound is administered orally.

20. The method of claim 19, wherein the compound is administered in a dose of from one to three $g/m^2$.

21. The method of claim 20, wherein the dose is administered two or three times per day.

22. A pharmaceutical composition comprising the compound of claim 1 in an amount effective to treat a disorder characterized by cerebral metabolic energy failure or diminished mitochondrial energy reserve capacity in a mammalian subject and a pharmaceutically acceptable carrier, wherein the disorder is:

(i) a neurological disorder;

(ii) a neuromuscular disorder;

(iii) a heart failure; or (iv) a primary genetic mitochondrial disease.

23. A method for producing 5'-O-Acetoacetyl-2',3'-di-O-acetyluridine, comprising:

(a) mixing 2',3'-O-isopropylideneuridine and 2,2,6-trimethyl-4H-1,3-dioxin-4-one in dimethylformamide under conditions to produce 5'-O-acetoacetyl-2',3'-O-isopropylideneuridine;

(b) mixing the 5'-O-acetoacetyl-2',3'-O-isopropylideneuridine from (a) with aqueous acetic acid under conditions to produce crude 5'-O-Acetoacetyluridine;

(c) dissolving the crude 5'-O-Acetoacetyluridine from (b) in a mixture of dichloromethane and pyridine, and then adding acetic anhydride and stirring for several days;

(d) to the mixture resulting from (c), switch the solvent to ethyl acetate and neutralize with saturated $NaHCO_3$ to yield crude 5'-O-Acetoacetyl-2',3'-di-O-acetyluridine.

24. The method of claim 23, wherein (a) is performed at a temperature of from 90° C. to 110° C.

25. The method of claim 23, wherein (b) is performed at a temperature of from room temperature to 75° C.

26. The method of claim 25, wherein (b) is performed at a temperature of about 65° C.

27. The method of claim 23, wherein (c) is performed at about room temperature.

28. The method of claim 23, further comprising purifying the crude 5'-O-Acetoacetyl-2',3'-di-O-acetyluridine from (d) to yield purified 5'-O-Acetoacetyl-2',3'-di-O-acetyluridine.

29. A compound, 5'-O-Acetoacetyluridine.

* * * * *